United States Patent [19]

Dodd

[11] Patent Number: 4,680,957
[45] Date of Patent: Jul. 21, 1987

[54] NON-INVASIVE, IN-LINE CONSISTENCY MEASUREMENT OF A NON-NEWTONIAN FLUID

[75] Inventor: Stephen C. Dodd, Thorndale, Pa.

[73] Assignee: The Davey Company, Jersey City, N.J.

[21] Appl. No.: 729,687

[22] Filed: May 2, 1985

[51] Int. Cl.⁴ ............................................ G01N 11/08
[52] U.S. Cl. ........................................... 73/55; 137/3
[58] Field of Search ................. 73/56, 55, 54; 162/49, 162/258, 263; 137/3, 92; 13/4

[56] References Cited

U.S. PATENT DOCUMENTS

| | | | |
|---|---|---|---|
| 2,233,561 | 3/1941 | Kalle . | |
| 2,302,327 | 11/1942 | Kehoe et al. . | |
| 2,437,715 | 3/1948 | Thorp et al. | 162/258 |
| 2,618,966 | 11/1952 | Karlsson | 73/54 |
| 2,626,786 | 1/1953 | McGlothlin . | |
| 2,627,788 | 2/1953 | Staege | 162/254 |
| 2,896,658 | 7/1959 | Allen et al. | 73/56 |
| 2,948,145 | 8/1960 | Eolkin | 73/54 |
| 2,973,000 | 2/1961 | Pearson . | |
| 3,035,967 | 5/1962 | Sacksen et al. | 162/191 |
| 3,148,533 | 9/1964 | Trimbey . | |
| 3,295,866 | 7/1965 | Coats | 280/479 R |
| 3,465,573 | 9/1969 | Shoemaker | 73/54 |
| 3,526,281 | 9/1970 | Cowan . | |
| 3,589,980 | 6/1971 | Salomon . | |
| 3,705,078 | 12/1972 | Shinohara | 162/198 |
| 3,720,097 | 3/1973 | Kron | 73/55 |
| 3,924,840 | 12/1975 | Nelson, Jr. | 324/140 D |
| 3,962,581 | 6/1976 | Zimmerman | 250/341 |
| 4,053,353 | 10/1977 | Leffler . | |
| 4,148,214 | 4/1979 | Madsen . | |
| 4,148,215 | 4/1979 | Hofstetter, Jr. . | |
| 4,165,632 | 8/1979 | Weber et al. | 73/55 |
| 4,171,916 | 10/1979 | Simms et al. | 356/366 |
| 4,179,332 | 12/1979 | Ilmoniemi et al. . | |
| 4,241,602 | 12/1980 | Han et al. | 73/56 |
| 4,285,239 | 8/1981 | Heine | 73/434 |
| 4,407,698 | 10/1983 | Andersson et al. . | |
| 4,415,408 | 11/1983 | Greey . | |
| 4,495,798 | 1/1985 | Ehrgott | 73/54 |

OTHER PUBLICATIONS 347361 54-07361 Transport Characteristics of High--Consistency Wood-Fiber Suspensions Kalinin, N. N.; Sidcrow, M. A.; Khramov, Yu. V.; Kiprianov, A. I., Izv. VUZ, Lesnoi Zh. No. 5: 91-96 (1982), [Russ.] 4 Fig., 11 Ref., 2 Tab. Document Type: Journal Article, Languages: Russian.
Bird et al., Transport Phenomena, Dept. of Chemical Engineering, Univ. of Wisconsin, John Wiley & Son Inc., 1965.
Waller, Measurement & Control of Paper Stock Consistency, Instrument Society of America, 1983.

Primary Examiner—Stewart J. Levy
Assistant Examiner—Hezron E. Williams
Attorney, Agent, or Firm—Hall, Myers & Rose

[57] ABSTRACT

Provided herein is an in-line, non-invasive device and method for calculation of consistency of a non-Newtonian fluid flowing in a laminar manner through a non-rotating conduit where the consistency is calculated directly from a power-law model equation employing as independent variables pressure head loss over a specific distance and the bulk velocity of the fluid.

20 Claims, 2 Drawing Figures

Microfiche Appendix Included
(1 Microfiche, 18 Pages)

NON-INVASIVE, IN-LINE CONSISTENCY MEASUREMENT OF A NON-NEWTONIAN FLUID

FIELD OF THE INVENTION

This invention relates to fluid consistency measurement and, more particularly, to a non-invasive, in-line means and method for calculating consistency of a non-Newtonian, two component fluid such as paper stock.

BACKGROUND OF THE INVENTION

High speed, automated processing machines now employed in mills for paper manufacture require a high degree of consistency control. This control is necessary because variations in feedstock consistency may result in dramatic changes in the finished product. If not strictly monitored, such variations will destroy the uniformity and, therefore, the desirability of the finished paper product.

In order to monitor feedstock consistency, thereby minimizng such variations, a number of devices have been adopted in the paper industry. Devices dedicated to this purpose may be categorized as four primary types: non-invasive, in-line; invasive, in-line; non-invasive, off-line; and invasive, off-line.

Turning first to the non-invasive, invasive distinction, the non-invasive devices are generally more modern and contemplate the use of ultrasound or light, which generally detect consistency variations by comparative analysis with known standards. Such devices are exemplified by that illustrated in U.S. Pat. No. 4,171,916. In-line, non-invasive measuring devices dedicated to other purposes are also known. For example, Heine, in U.S. Pat. No. 4,285,239, describes a device for determining the density of flowing slurry materials.

Returning to consistency measuring devices, others employ non-invasive pressure transducers to make comparative analysis like that depicted in Staege, U.S. Pat. No. 2,627,788. The most common invasive type of device is characterized by an impeller. Impeller devices often are based on comparative driving shaft torque measurements to indicate fluctuating consistency of stock (See Coats, U.S. Pat. No. 3,155,866). Another type of impeller-based measuring device is illustrated in Madsen, U.S. Pat. No. 4,148,214, having pressure transducers located in close proximity to the impeller blades to detect pressure differences and, consequently, consistency variations. Impeller-based devices are also employed in off-line devices. Cowan, in U.S. Pat. No. 3,528,281, employs an impeller to draw fluid from a conduit into a sample tube where the variable volume flow is used to determine consistency. Staege constitutes an off-line device which employs non-invasive apparatus for paper stock pressure measurement.

All of the above-described consistency measuring devices determine consistency by empirical comparative analysis. The impeller-based devices are recognized to give repeatable measurements and, if associated with a control device, are generally capable of regulating consistency to ±0.05%. However, these devices suffer from two noted shortcomings. First, although repeatable, the measurements are often inaccurate. Secondly, impeller-type devices often become snagged with string, other strong fibrous materials or fabric pieces. Hence, frequent cleaning and recalibration are the rule. The non-invasive wave energy frequency type (ultrasound, light, etc.) often produce less repeatable measurements (±0.1%) due to fluctuations in fiber length and flow rate. Excepting Coats, all recognize a relationship between consistency and pressure and/or velocity but determine the relationship in comparative empirical analysis.

In view of the noted shortcomings of currently available consistency measuring and control devices and the considerable efforts to perfect such devices, the need still exists for accurate, repeatable consistency measurement.

SUMMARY OF THE INVENTION

It is an object of this invention to provide a means and method for determining the consistency of a flowing, non-Newtonian, two component fluid.

It is another object of this invention to permit repeatable, accurate calculation of a numerical consistency value for a flowing multi-component fluid.

Another object of this invention is to generate an absolute consistency value for a flowing non-Newtonian fluid using non-invasive, in-line means and methods.

It is another object of this invention to measure consistency of a non-Newtonian fluid with a device employing a minimum of moving parts.

Still another object of this invention is to provide a means and method for non-invasive, in-line, accurate measurement of consistency according to a power-law model for a non-Newtonian multi-component fluid flowing through a conduit.

An additional object of this invention is to provide a means and method for calculating consistency which is not substantially influenced by freeness, density, solids content or pH of the non-Newtonian fluid.

Yet another object of this invention is to facilitate control of the consistency of a non-Newtonian fluid during processing.

A more narrow object of this invention is to provide a means and method for calculating the consistency of flowing paper stock using a power-law based algorithm employing measurements of pressure loss and flow rate as well as controlling the consistency with a responsive means to the calculation.

Certain of these objects are satisfied by a method for measuring and monitoring the consistency of a fluid having at least two components and flowing through a conduit, comprising the steps of providing a fluid feedstock into a conduit of a selected cross-sectional configuration in a manner where the fluid flows through the conduit in a non-turbulent manner, sensing the velocity of the fluid feedstock flowing through the conduit, sensing the pressure of the fluid at two points separated by a selected distance along the conduit, determining the pressure differential between the two points, inputting values of the pressure differential, distance, dimensions and velocity into a calculating device and, calculating the consistency of the fluid according to a power-law algorithm applicable to the fluid and the cross-sectional geometry of the conduit.

Still other objects of this invention are satisfied by an apparatus for monitoring the consistency of a liquid composed of at least two components simulating a non-Newtonian fluid when flowing in a substantially laminar manner through a conduit of a given cross-sectional configuration, comprising means for flowing said fluid in a substantially laminar manner through the conduit, means for measuring the bulk velocity of the fluid flowing through the conduit, said measuring means producing a signal representative of the bulk velocity, at least two means at remotely spaced points for sensing the pressure of the fluid in the conduit where each sensing means produces a signal representative of the pressure at each point and, means for directly calculating the consistency of the liquid according to a power-law model requiring as independent values, said representative signals.

This invention provides a wholly novel and unique solution for determining consistency of non-Newtonian fluid flowing in a laminar manner through a conduit. The invention is primarily directed for use with paper stock but may be applied to most any pseudoplastic or dilatant non-Newtonian fluid. Both the means and methods presented herein contemplate in-line, non-invasive consistency determination for monitoring or control of consistency. Rather than comparing consistency values against known standard solutions or establishing random calibration, this invention accurately ascertains an actual numerical value of consistency. The consistency calculation requires the measurement of only two independent variables from a non-turbulent flowing fluid; pressure head loss over a specifically selected distance and bulk velocity. These two variables are plugged into a power-law based algorithm which produces a real value of consistency. The algorithm, being programmed into a calculating device such as a computer, allows for a direct determination of the consistency value, and produces a signal which may be displayed for monitoring purposes or may be associated with responsive control apparatus for maintaining the consistency of the paper stock.

Unlike the previous consistency measuring systems, the in-line, non-invasive features enhance the reliability of the consistency values calculated according to this invention. The apparatus does not rely on an invasive impeller, the operation of which can vary due to snagging of stringy and fibrous materials. As will become apparent, the contemplated apparatus has a minimum of moving parts, thus eliminating mechanical breakdown and increased reliability. Furthermore, the invention provides repeatable, accurate consistency values without the need for continuous recalibration against comparative standards.

It is evident that the invention provides a means and method lending itself to automated systems involving processing of non-Newtonian fluids. Automatic calculation of a true numerical value of consistency is clearly superior to tedious, generally non-repeatable hand measurement and the comparative methods elaborated upon above. The fast, repeatable, accurate means and methods of this invention are highly desirable for monitoring quality and automated control of fluid consistency. Particularly in the context of computerized consistency control, virtual instantaneous response to consistency variations is assured; hence, greater adherence to product specifications and enhanced product quality.

DETAILED DESCRIPTION OF THE EMBODIMENTS

Preliminarily, it must be noted that the below-described apparatus represents one means for practice of this invention. It can be readily appreciated, however, that the elementary apparatus disclosed herein may be incorporated into more complex systems in a variety of embodiments. A person of ordinary skill in the fluid property measuring art, without undue experimentation, can generate equipments dedicated for particular fluids in particular situations. For the purpose of this application it is neither necessary nor desirable to provide an exhaustive list of possibilities. Therefore, apparatus for determining the consistency of paper stock, a non-Newtonian, pseudoplastic fluid, flowing through a non-rotating, circular conduit is described, in detail, to illustrate the invention.

It is necessary to first point out that the below-described apparatus is useful only when associated with the below-described algorithm. It is through the algorithm that fluid consistency is calculated from the measurements generated by the apparatus. The consistency of a multi-component, solid/liquid non-Newtonian fluid cannot be accurately determined without its use, except by laboratory experiments.

Secondly, it has been observed that determination of consistency values according to this invention is seriously flawed when paper stock flows in a turbulent manner in a conduit. Where flow becomes non-laminar, the means and methods disclosed herein do not work. If plotting the log of bulk velocity against the log of pressure head loss, the curve rises at a constant slope until turbulance is experienced. It is in this range of constant slope, that the invention is intended to operate. Employing engineering terms, the Reynolds number for heterogeneous fluids, $Re'$, should not exceed 70 in order to achieve laminar flow characteristics. A detailed description of these Reynolds numbers is found in TAPPI (Technical Association of the Pulp and Paper Industry) Vol. 33, No.9, A Study of the Pipe Friction Losses of Paper Stock Suspension, an article by Brecht and Heller.

Thirdly, in general, paper manufacture uses paper stock solutions having a consistency between 2-5%. If lesser consistency material is employed, it flows faster in order to maintain a constant flow on a dry basis and, therefore, may give rise to turbulence. In the practice of the invention, one solution to overcome this problem is simply to increase the conduit radius, thereby reducing the velocity of the fluid.

Figure 1:
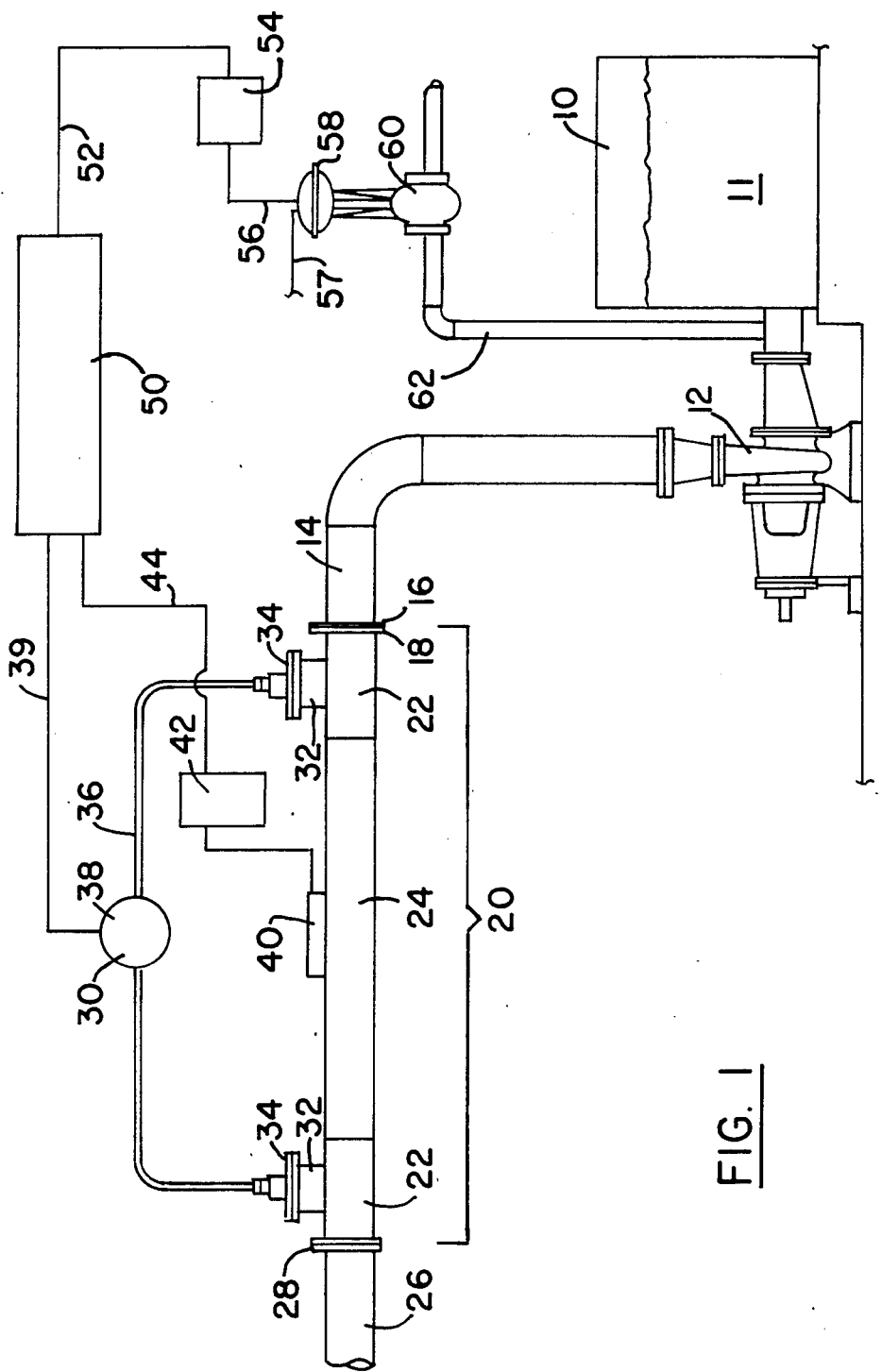
FIG. 1 is a partial schematic representation of the apparatus used in the practice of the invention.

Now referring to FIG. 1, paper stock 11, conventionally having a consistency ranging between 3-4%, is drawn from stock chest 10 by pump unit 12 and into horizontal ingress pipe 14. Ingress pipe 14 has a substantially constant diameter and is at least eight pipe diameters in length. Like all remaining conduit sections, Pipe 14 should be manufactured of corrosion resistant materials. Stainless Steel 304-L pipes produced by Felker Bros. Mfg. of Marshfield, Wis. prove suitable for this purpose. Pipe 14 further incorporates exterior flange member 16 which cooperates and mates with spool flange 18 to attach spool 20 to pipe 14. Spool 20, the primary apparatus of this invention, incorporates T-members 22, located at opposite ends thereof and elongated central section 24 disposed therebetween. The length of spool 22 may vary to most any desired length and the diameter may range between ½-24 inches, depending on the flow rate necessary to insure laminar flow. For example a four inch diameter, twelve foot long spool 20 required a flow rate of approximately 6-7 feet/sec of 3-4% consistency paper stock in order to utilize 30 tons of solids in one day.

Furthermore, it is critical to the proper function of this invention that turbulance and other undesirable flow phenomena be minimized. Hence, it is important that spool 20 have a substantially smooth, continuous, constant diameter interior surface. It is also desirable that ingress pipe 14 and egress pipe 26 possess substantially similar characteristics.

Turning briefly to egress pipe 26 it also bears cooperating, mating flanging 28 for attachment to spool 20. Because pipe 26 is located downstream from spool 20, it is preferred, at a minimum, that pipe 26 have a length of at least 4 pipe diameters because the internal geometric configuration requirements are lesser than those for ingress pipe 14. Flow discontinuities created by internal geometric alterations will not have as pronounced an effect on stock 11 as it flows through spool 20.

Referring back to spool 20, it features differential pressure transmitter assembly 30 including diaphragm type sensing interfaces 32, pressure seals 34 and transducer 38. Interfaces 32 comprise extended head pressure seals 34, like the Foxboro Model 823EP-IM1SA2KD from the Foxboro Company of Foxboro, Mass. The seals incorporate diaphragms (interfaces 32) of 316 stainless steel, a low coefficient of thermal expansion pressure seal fluid and an operating temperature range of $-35°$ to $180°$ F. Each of T-members 22 serve as a housing for each of seals 34 and interfaces 32. It is important, in order to minimize flow turbulence discontinuities that interfaces 32 substantially match the radius of the interior wall of spool 20.

Interfaces 32 sense the absolute pressure of paper stock flowng through spool 20 at two remote points. It has been observed that to increase the accuracy of the ultimately obtained consistency value, the distance between these points must be increased. The pressure signals corresponding to the fluid pressure at each point are transmitted from seals 34 to differential pressure transducer 38 via hydraulic capillaries 36. Transducer 38 converts sensed differential pressure value into a proportional 4–20 ma analog signal. This signal is then inputted into data acquisition system 50 over wire 39.

Spool 20 also features flow transducer 40; a clamp-on, waterproof, high-frequency, ultra-sonic transducer which is capable of operation at temperatures between $-40°$ to $180°$ F. and detects flow rate of as little as 0.5 ft/s and slurries down to 25 parts per million. Transducer 40 generates ultrasonic wave energy, directing it into flowing stock 11 and detects the quantum of reflected energy. A signal corresponding to the reflected energy is fed to transmitter 42 which determines the doppler shift caused by the flow rate of stock 11. Transmitter 42 then generates a 4–20 ma analog signal proportional to the stock's bulk velocity that is transmitted to data acquisition system 50 over wires 44. The Dynasonic Model 4FT-30013-T500 Hf flowmeter assembly manufactured by Dynasonic, Inc., Naperville, Ill., incorporates both a transducer and transmitter meeting the above-described preferred requirements.

The signals fed into data acquisition system 50 represent the pressure drop (pressure head loss) over the length of spool 20 and the bulk velocity of stock 11. Data acquisition system 50 employs the below-described algorithm to calculate the consistency of stock 11 using the data generated from the transducers. Although a measurement of stock consistency may be of value for quality control monitoring purposes, it is preferred to associate data acquisition system 50 with a consistency control system. Such a control system is now described.

Ideally, the control system is provided with a means to establish a particularly desired consistency. The consistency is then set at that value which is inputted into data acquisition system 50. Once inputted, the system is able automatically to calculate and compare the consistency of stock 11 with the preset value and make any required adjustments.

A 4–20 ma signal representing the differential between the actual and set consistency values is transmitted over wires 52 to Standard I/P converter 54 such as the Dynasonic's Model 512000. Converter 54 receives the signal and converts it to a pneumatic signal of between 3–15 p.s.i. The pressurized air travels from converter 54 to valve positions 58 through copper tube 56 which positions the valve porportionally in response to the aforesaid pneumatic signal. The valve is actually moved by supply air 57 at 80 psi. In this particular arrangement, a Foxboro Power Positioner meeting the following specifications: air supply: max. 150 p.s.i., air delivery: 7.4 scfm at 60 p.s.i., relay bleed: 0.75 scfm at 50 p.s.i., accuracy: 1% of stroke, sensitivity: 1 inch water signal pressure and a temperature range: $-20°$ to $160°$ F., was employed. The positioner is attached to the stem of and controls the movement of valve 60.

Stainless steel valve 60 is characterized by a V-seat insert and an air cylinder mount such as the Fabri-Valve Knife Gate #37R-316-V-HO1 available from Fabri-Valve of Portland, Oreg. Valve 60 controls the quantity of water flowing into pipe 62. Pipe 62 is connected to pump unit 12 so the amount of water flowing into pump 12 governs the consistency of stock 11 pumped into pipe 14. Consequently, the consistency of stock 11 is automatically and continuously stabilized by this feedback control system.

The summarize the "hardware" employed in the practice of the invention, pump 12 moves stock 11 to spool 20 where in-line, non-invasive measurement of pressure head loss and flow rate is made. The generated signals are fed into data acquisition system 50 where the measurements are calculated by the below-described algorithm to determine consistency. Where the consistency value so obtained differs from a pre-set value, a proportional signal generated by system 50 is fed into converter 54 which governs control valve 60 thereby controlling water flow quantity into pump 12 and, accordingly, the consistency of stock 11.

Figure 2:
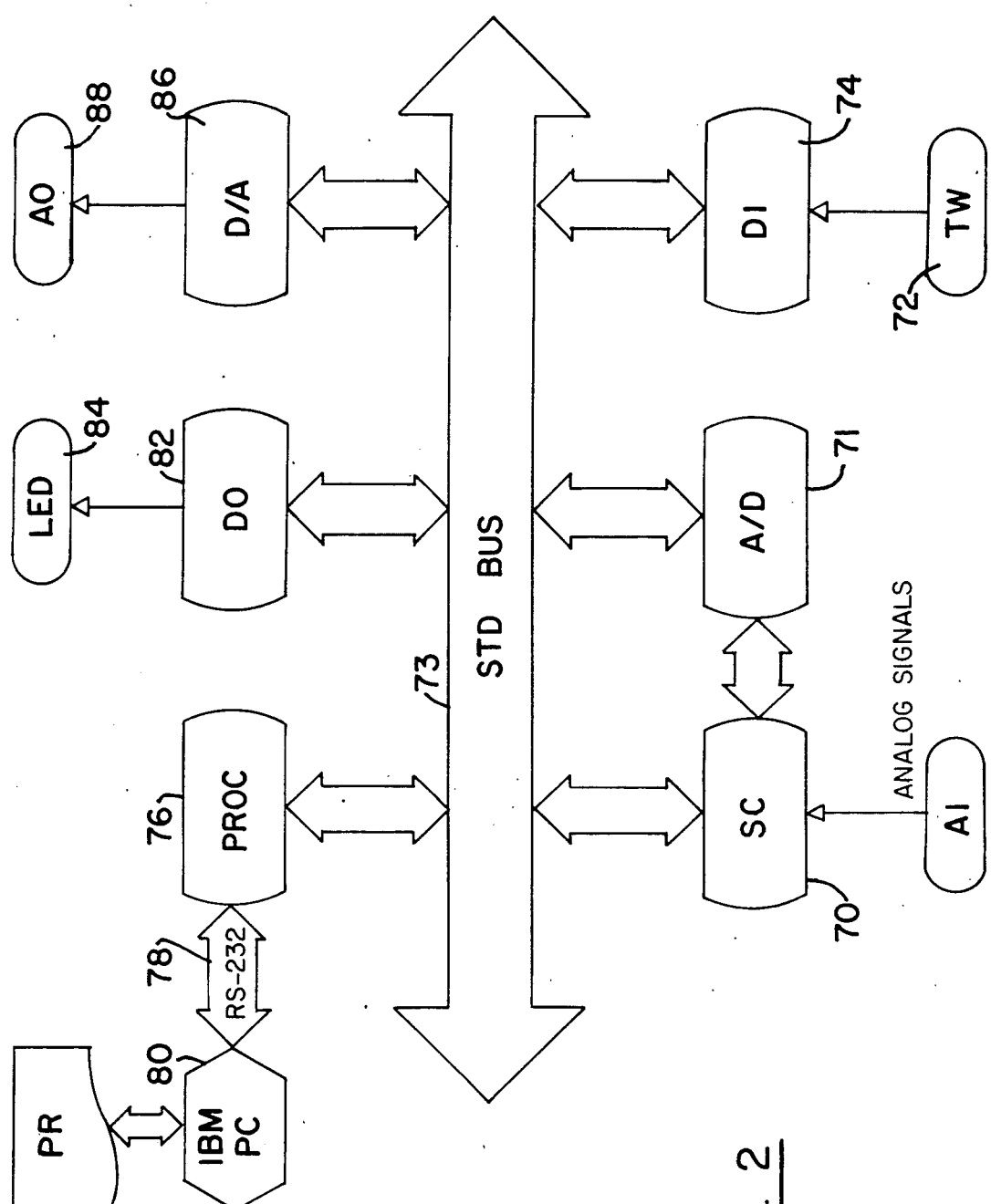
FIG. 2 is a schematic representation of the data acquisition and control system of this invention.

At this point it is desirable to briefly describe the operation of data acquisition system 50. A schematic diagram of this operation is found in FIG. 2. Analog signals from the velocity transmitter 42 and differential pressure transmitter 38, are received by the signal conditioning module 70 and converted to digital signals by digital conversion module 71. The constant parameters $\alpha$, $\beta$, n, R & L (identified below) as well as a desired consistency setpoint are keyed in by conventional thumbweels 72 to digital input module 74. Processor module 76 which has been programmed with the program found in Appendix A submitted herewith via RS-232 serial communications cable 78 and computer 80 (an IBM-PC TM,) receives the values stored in module 71 and module 74 via standard bus 73 (a commercially available device comprising a set of parallel lines for transmission of digital information between computer components) and calculates the consistency according to the below-described algorithm. This consistency value, as well as the other signals, are then sent to digital output module 82 which in turn displays the signals and consistency on conventional LED's 84. If a control system is associated with the consistency determining assembly, processor 76 also compares the value of the consistency with the consistency setpoint and calculates the proper control action using standard PID (Proportional, Integral, Derivative) software. The control action signal is transmitted via BUS 73 to digital-/analog converter module 86 which outputs analog signal 88 (52 in FIG. 1) to I/P converter 54 and finally valve 60.

Referring now to the heart of the invention, it is an algorithm which permits consistency of a fluid to be calculated as an absolute value employing only pressure head loss and flow rate as independent variables. A summary of the derivation of the algorithm is now provided.

The equation of motion which describes (in cylindrical coordinates) a fluid in laminar flow at steady-state through a non-rotating circular pipe is described on page 85 of Bird, R. B., Stewart, W. E. and Lightfoot, E. W., "Transport Phenomena," John Wiley & Sons, Inc., New York 1960.

$$\frac{\delta \bar{P}}{\delta z} = \frac{-1}{r} \frac{\delta}{\delta r} (r\tau_{rz}) + \rho g_z \tag{1}$$

or $$\frac{\delta P}{\delta z} = \frac{1}{r} \frac{\delta}{\delta r} (r\tau_{rz}) \tag{2}$$

where
$P = \bar{P} - \rho g_z$ is the absolute pressure
r = radial dimension
z = length dimension
and
$\tau_{rz}$ is the shear force.

For water, the shear force is a linear function of the velocity gradient in the pipe:

$$\tau_{rz} = -\mu \frac{dV_z}{dr} \tag{3}$$

$V_z$ = velocity
$\mu$ = viscosity (constant)

A fluid which obeys Equation 3 is called a Newtonian fluid. The shear force of paper stock, however, is not a linear function of the veolocity gradient. The "apparent viscosity" is affected by the consistency (% solids) of the paper stock. The Duffy Correlation, below, described and discussed in Waller, M. H., "Measurement and Control of Paper Stock Consistency", Instrument Society of America-Monograph 5, (1983), relates the head loss of paper stock in a pipe to the consistency and velocity, using an elastic deformation of the fiber network model.

$$\frac{dH}{L} = KC^\alpha V^\beta D^\gamma \tag{4}$$

where,
dH/L = head loss/length of pipe
C = consistency
V = bulk velocity
D = pipe diameter
K, $\alpha$, $\beta$, and $\gamma$ = suitable coefficients This equation has been compared with data, and values of K, $\alpha$, $\beta$ & $\gamma$ have been determined to give the best correlation. This correlation is used quite often in calculating pressure drops in the design of paper stock flow systems. See pg. 247–252, Duffy, G. G., "How to Determine Pipe Friction Loss for the Design of Stock Piping Systems," TAPPI Engineering Conference Proceedings Book 2, 1979.

The shear force of non-Newtonian fluids, such as paper stock, is subjected to a power law relationship like that presented by the Ostwald-de Waele model:

$$\tau_{rz} = -m \left| \frac{dV_z}{dr} \right|^{n-1} \frac{dV_z}{dr} \tag{5}$$

$m = .418 \text{ lb}_f - s^n/\text{ft}^2$ $n = .575$ $-m \left| \frac{dV_z}{dr} \right|^{n-1}$ = apparent viscosity For fluids with a value of n − 1, the behavior is said to be pseudoplastic. Metzner Advances in Chemical Engineering, Vol. I, Academic Press, New York (1956), pg 163, found that a 4% paper stock solution had the foregoing values of m and n. Thus, paper stock can be considered a pseudoplastic fluid.

Equations 2 and 5 completely describe the flow of any pseudoplastic (including paper stock) in a non-rotating, circular pipe. It is evident that fluids other than paper stock require different m and n values. Such values may be determined from appropriate experimentation or may be available from the literature. To determine relationship between the "apparent viscosity" and consistency, Equation 5, found on page 11 of the Bird publication, is substituted into Equation 2 and solved for the velocity profile $V_z(r)$:

$$V_z(r) = \left( \frac{n}{n+1} \right) \left( \frac{\Delta P}{2mL} \right)^{\frac{1}{n}} \left[ 1 - \left( \frac{r}{R} \right)^{\frac{n+1}{n}} \right] R^{\frac{n+1}{n}} \tag{6}$$

$V_z(r)$ = velocity profile
$\Delta P$ = pressure change
m = constant
n = constant
R = radius of pipe
L = length of pipe The next step is to determine the bulk velocity of the fluid by integrating the velocity profile over the cross-sectional area, and dividing by the cross-sectional area:

$$<V_z> = \left( \frac{\Delta P}{2mL} \right)^{\frac{1}{n}} R^{\frac{n+1}{n}} \left( \frac{n}{3n+1} \right) \tag{7}$$

$<V_z>$ = bulk velocity
R = radius of pipe

Finally, the head loss is determined by integrating the local rate of dissipation of mechanical energy over the volume of a pipe of length L as described on page 215 of the Bird publication:

$$E_v = - \int_V (\tau : \nabla v) dv \tag{8}$$

V = volume of pipe length L
where, $\bar{E}_v$ is the friction loss and $\tau:\nabla v$ is the rate of irreversible conversion to internal energy. When solving Equation 8, with the power law model described in Equation 5, the resulting equation (per unit mass) is (see pg. 236 of Bird):

$$\bar{E}_v = \frac{2mL <V_z>^n}{\rho R^{n+1}} \left(3 + \frac{1}{n}\right)^n \quad (9)$$

$\rho$ = density

Examining paper stock friction loss data correlated by Brecht and Heller (TAPPI, Vol. 33(9), Pg. 144, (1950)) supra. and correlating it with Equation 9, the following relationship resulted:

$$m = \alpha C^\beta \quad (10)$$

Pressure loss data is compared to m using Equations 9 and 10 for various pipe sizes, velocities and consistencies.

Table 1 compares data obtained from Brecht and Heller with that obtained from the power law model.

TABLE 1

| C % | $<V_z>$ ft/s | D inches | $H_f$ ft/100 ft (Article) | $\bar{E}_v$ ft/100 ft. (from Equation 9) |
|---|---|---|---|---|
| 2.0 | 2.0 | 6.0 | 5.16 | 5.15 |
| 2.0 | 4.0 | 6.0 | 6.63 | 6.75 |
| 3.0 | 2.0 | 6.0 | 11.02 | 10.93 |
| 4.0 | 3.4 | 6.0 | 23.10 | 23.16 |
| 3.0 | 4.0 | 4.0 | 24.58 | 25.43 |
| 4.0 | 5.1 | 4.0 | 45.96 | 47.65 |
| 4.5 | 3.8 | 4.0 | 51.80 | 53.16 |
| 2.0 | 4.0 | 8.0 | 4.47 | 4.49 |
| 3.0 | 4.0 | 8.0 | 9.65 | 9.61 |
| 4.0 | 8.0 | 8.0 | 21.39 | 21.64 | where $\alpha = 0.0244$, $\beta = 1.88$, $n = 0.39$ and $L = 100$ ft.

It is readily apparent that the power-law model reproduces actual friction loss data accurately. To illustrate the relationship of consistency to bulk velocity and the pressure drop in the pipe, Equation 10 is substituted into Equation 7 and consistency isolated. The resulting equation is:

$$C = \left(\frac{\Delta P}{2\alpha L}\right)^{\frac{1}{\beta}} \frac{R^{\frac{n+1}{\beta}}}{<V_z>^{n/\beta}} \left(\frac{n}{3n+1}\right)^{\frac{n}{\beta}} \quad (11)$$

Thus, an equation is obtained for determining the consistency of a pseudoplastic in a non-rotating, circular pipe having as the only independent variables, pressure head loss over a specific length and the fluid flow rate. Employing the above-described apparatus, these variables are determined and, therefore, the fluid consistency is calculable. The consistency calculation, in the above-described embodiment of the invention may be performed on the above described data acquisition system utilizing the program contained in Appendix B submitted herewith.

The determination of consistency of a non-Newtonian fluid flowing through a conduit is not limited to the specific geometry of the conduit. The detailed derivation of consistency flowing through a pipe having a circular cross-section is applicable to other geometries albeit subject to some modification. For example, the alternative expression for calculating the consistency of a non-Newtonian fluid through a rectangular, slotted spool 20 is described below. First it should be noted, however, that the apparatus in this embodiment should possess the same characteristics as those described above for a circular conduit, i.e. smooth, continuous interior surface, etc.

Moving now to the establishment of the algorithm necessary for consistency calculation for the slotted geometry, the equation of motion describing in rectangular coordinates the laminar flow of a fluid at steady-state through a non-rotating, rectangular slotted conduit is:

$$\frac{\delta \bar{P}}{\delta z} = -\frac{\delta \tau_{xz}}{\delta x} + \rho g_z \quad (12)$$

or $$\frac{\delta P}{\delta z} = \frac{\delta \tau_{xz}}{\delta x} \quad (13)$$

where $P = \bar{P} - \rho g_z$ is the absolute pressure and $\tau_{xz}$ is the shear force.

The equivalent of Equation 5, but written in rectangular coordinates is:

$$\tau_{xz} = -m \left|\frac{dV_z}{dx}\right|^{n-1} \frac{dV_z}{dx} \quad (14)$$

Equation 14 is then substituted into Equation 13 and the resulting expression is solved for the velocity profile $V_z(x)$:

$$V_z = \frac{n}{n+1} \left[\frac{P_o - P_L}{mL}\right]^{\frac{1}{n}} \left(1 - \left(\frac{x}{B}\right)^{\frac{n+1}{n}}\right) B^{\frac{n+1}{n}} \quad (15)$$

Next, the bulk velocity is determined by integrating the velocity profile over the cross-sectional area, and then dividing by the cross-sectional area.

$$<V_z> = \left(\frac{\Delta P}{mL}\right)^{\frac{1}{n}} \left(\frac{n}{n+1}\right) \left(1 - \frac{n}{2n+1}\right) B^{\frac{n+1}{n}} \quad (16)$$

Substituting Equation 10 from above, into Equation 16, consistency for a fluid flowing through a rectangular, slotted conduit is then expressed as:

$$C = \left(\frac{\Delta P}{\alpha L}\right)^{\frac{1}{\beta}} \frac{B^{\frac{n+1}{\beta}}}{<V_z>^{\frac{n}{\beta}}} \left(\frac{n}{n+1}\right)^{\frac{n}{\beta}} \left(1 - \frac{n}{2n+1}\right)^{\frac{n}{\beta}} \quad (17)$$

It should now be apparent to one of ordinary skill in the art that consistency determinations for other conduit geometries are easily solvable by employing the equation of motion for a power-law type fluid, in laminar flow, and at steady-state. Hence, the consistency of a fluid flowing through any non-rotating conduit is determinable by variation of the proper coordinate system as applied to the above-identified equations. As two such systems have been described, it is not believed to be necessary to elaborate further on such variations for the purpose of this application.

This invention also contemplates development of derivative information employing the calculated consistency values. For example, having the actual value of consistency, the tons per day of paper stock 11 flowing through spool 22 can also be calculated using the following equation.

$$S = 84.66 <V_z> R^2 C \qquad (18)$$

where:
S = tons/day
R = radius of pipe (ft)
C = consistency (%)
$<V_z>$ = bulk velocity (ft/s)

Once given the above disclosure, various other modifications and improvements will become apparent to the skilled artisan. As such, they are considered to be part of the invention, the scope of which is to be determined by the following claims:

What is claimed is:

1. A method for measuring and monitoring the consistency of a fluid having at least two components and flowing through a conduit, comprising the steps of:
   (a) providing a fluid feedstock into a conduit in a manner where the fluid flows through the conduit in a substantially non-turbulent manner,
   (b) sensing the velocity of the fluid feedstock flowing through the conduit,
   (c) sensing the pressure of the fluid at two points separated by a selected distance along the conduit,
   (d) determining the pressure differential between the two points,
   (e) inputting values of the pressure differential, distance and velocity into a calculating device, and
   (f) calculating the consistency of the fluid according to a power-law algorithm applicable to the cross-sectional geometry of the conduit.

2. A method according to claim 1 further comprising the steps of providing a non-Newtonian, solid bearing liquid feedstock and flowing said feedstock to a receiving apparatus.

3. A method according to claim 2 wherein the feedstock is paper stock behaving as a pseudoplastic and the receiving apparatus is a means for forming a solid paper product.

4. A method according to claim 2 further comprising the steps of setting a desired consistency value and maintaining fluid feedstock at the desired consistency by adjusting the concentration of solids in the fluid in response to changes in the calculated consistency value.

5. A method according to claim 1 further comprising the steps of displaying the calculated consistency value and adjusting the concentration of one of the components relative to the other to control the fluid consistency.

6. A method of controlling the consistency of a liquid comprised of at least two components and which simulates a pseudoplastic when flowing in a substantially laminar condition through a substantially circular conduit, the steps comprising:
   (a) flowing said liquid in a substantially laminar condition through the conduit,
   (b) measuring the bulk velocity of said fluid as it flows through said conduit,
   (c) measuring any change in the pressure of the fluid in said conduit as said fluid flows between two points spaced a distance L from each other,
   (d) adjusting the level of a component in the liquid to thereby control the consistency of the liquid in response to the following formula:

$$C = \left(\frac{\Delta P}{2\alpha L}\right)^{\frac{1}{\beta}} \frac{R^{\frac{n+1}{\beta}}}{<V_z>^{n/\beta}} \left(\frac{n}{3n+1}\right)^{\frac{n}{\beta}}$$

where C = consistency (%)

7. A method of controlling the consistency of a liquid comprised of at least two components and which simulates a pseudoplastic when flowing in a substantially laminar condition through a conduit of a slotted cross-sectional configuration, the steps comprising:
   (a) flowing said liquid in a substantially laminar condition through the conduit of a slotted cross-sectional configuration,
   (b) measuring the bulk velocity of said fluid as it flows through said conduit,
   (c) measuring any change in the pressure of the fluid in said conduit as said fluid flows between two points spaced a distance L from each other,
   (d) adjusting the level of a component in the liquid to thereby control the consistency of the liquid in response to the following formula:

$$C = \left(\frac{\Delta P}{\alpha L}\right)^{\frac{1}{\beta}} \frac{B^{\frac{n+1}{\beta}}}{<V_z>^{\frac{n}{\beta}}} \left(\frac{n}{n+1}\right)^{\frac{n}{\beta}} \left(1 - \frac{n}{2n+1}\right)^{\frac{n}{\beta}}$$

where C = consistency (%).

8. A product formed from a production method wherein the product is produced at least in part from a fluid or liquid wherein the consistency of the fluid or liquid is calculated by the method of claims 1, 6 or 7.

9. An apparatus for monitoring the consistency of a liquid composed of at least two components simulating a non-Newtonian fluid when flowing in a substantially laminar manner through a conduit of a given cross-sectional configuration, comprising:
   (a) means for flowing said fluid in a substantially laminar manner through the conduit,
   (b) means for measuring the bulk velocity of the fluid flowing through the conduit, said measuring means producing a signal representative of the bulk velocity,
   (c) at least two separate and spaced apart means for sensing the pressure of the fluid in the conduit where each sensing means produces a signal representative of the pressure at each point, and
   (d) means for directly calculating consistency of the liquid according to a power-law model requiring as independent values, said representative signals.

10. An apparatus according to claim 9 where the calculating means determines a value of consistency in response to a power-law model applicable to the cross-sectional geometry of the conduit.

11. An apparatus according to claim 10 where the conduit has a substantially circular cross-section and the calculating means employs the algorithm:

$$C = \left(\frac{\Delta P}{2\alpha L}\right)^{\frac{1}{\beta}} \frac{R^{\frac{n+1}{\beta}}}{<V_z>^{n/\beta}} \left(\frac{n}{3n+1}\right)^{\frac{n}{\beta}}$$

where C = consistency (%).

12. An apparatus according to claim 10 where the conduit has a substantially slotted cross-sectional geometry and the calculating means employs the algorithm:

$$C = \left(\frac{\Delta P}{\alpha L}\right)^{\frac{1}{\beta}} \frac{\frac{B^{\frac{n+1}{\beta}}}{<V_z>^{\frac{n}{\beta}}}}{\left(\frac{n}{n+1}\right)^{\frac{n}{\beta}} \left(1 - \frac{n}{2n+1}\right)^{\frac{n}{\beta}}}$$

where C = consistency (%).

13. An apparatus according to claim 9 further comprising means for establishing a desired consistency value of the liquid and control means for adjusting the consistency of the liquid to substantially equal the desired value.

14. An apparatus according to claims 9, 10, 11, 12 or 13 further comprising a non-invasive, in-line ultrasonic velocity measuring means, diaphragm type pressure sensing means, transducer means for generating a signal corresponding to the difference between the sensed pressure at the two points, and where said calculating means is a data acquisition and processing device adapted to receive said signals, calculate the consistency and transmit the calculated consistency value to said responsive means.

15. An apparatus according to claim 14 further comprising an ingress pipe for flowing the fluid into the conduit having a diameter substantially equal to that of the conduit and a length of at least eight diameters, and an egress pipe for flowing the fluid from the conduit having a diameter substantially equal to the diameter of the conduit and a length of at least four diameters.

16. An apparatus according to claim 15 where the conduit and said ingress and egress pipes are constructed from non-corrosive materials, possess a uniform interior geometry and have constant interior dimensions.

17. An apparatus according to claim 16 further comprising pumping means for flowing the liquid through the ingress pipe, conduit and egress pipe, said pump means having a first part for receiving the liquid and a second part for receiving a solvent employed to regulate the consistency of the liquid.

18. An apparatus for controlling the consistency of a liquid comprised of at least two components and which simulates a non-Newtonian fluid when flowing in a substantially laminar condition through a conduit of a given cross-sectional configuration, comprising:
  (a) means for flowing said liquid in a substantially laminar condition through the conduit of a given cross-sectional configuration,
  (b) means for measuring the bulk velocity of said fluid as it flows through said conduit,
  (c) means for measuring any change in the pressure of the fluid in said conduit as said fluid flows between two points spaced a distance L from each other,
  (d) means for adjusting the level of a component in the liquid to thereby control the consistency of the liquid in response to the formula:

$$C = \left(\frac{\Delta P}{2\alpha L}\right)^{\frac{1}{\beta}} \frac{R^{\frac{n+1}{\beta}}}{<V_z>^{n/\beta}} \left(\frac{n}{3n+1}\right)^{\frac{n}{\beta}}$$

where C = consistency (%).

19. An apparatus for controlling the consistency of a liquid comprised of at least two components and which simulates a non-Newtonian fluid when flowing in a substantially laminar condition through a conduit of a given cross-sectional configuration, comprising:
  (a) means for flowing said liquid in a substantially laminar condition through the conduit of a given cross-sectional configuration,
  (b) means for measuring the bulk velocity of said fluid as it flows through said conduit,
  (c) means for measuring any change in the pressure of the fluid in said conduit as said fluid flows between two points spaced a distance L from each other,
  (d) means for adjusting the level of a component in the liquid to thereby control the consistency of the liquid in response to the formula:

$$C = \left(\frac{\Delta P}{\alpha L}\right)^{\frac{1}{\beta}} \frac{\frac{B^{\frac{n+1}{\beta}}}{<V_z>^{\frac{n}{\beta}}}}{\left(\frac{n}{n+1}\right)^{\frac{n}{\beta}} \left(1 - \frac{n}{2n+1}\right)^{\frac{n}{\beta}}}$$

where C = consistency (%).

20. An apparatus according to claim 9 further comprising a responsive means for responding to the calculated consistency.

* * * * *